United States Patent [19]

Hughes et al.

[11] 4,386,032

[45] May 31, 1983

[54] LIQUID POLYISOCYANATE COMPOSITIONS

[75] Inventors: Jeffrey Hughes, Worsley; Kevin E. Keane, Middleton, both of England

[73] Assignee: Imperial Chemical Industries Limited, United Kingdom

[21] Appl. No.: 253,261

[22] Filed: Apr. 13, 1981

[51] Int. Cl.³ .......................................... C07C 119/048
[52] U.S. Cl. ...................... 260/453 AM; 260/453 SP; 260/453 AB; 560/27
[58] Field of Search .................. 260/453 AM, 453 SP; 560/27

[56] References Cited

U.S. PATENT DOCUMENTS 3,294,713 12/1966 Hudson et al. ......... 260/453 AM X
3,996,154 12/1976 Johnson et al. ..................... 252/312

FOREIGN PATENT DOCUMENTS 2513793 10/1975 Fed. Rep. of Germany .
2708820 9/1977 Fed. Rep. of Germany .
2241597 3/1975 France .
47-11390 11/1972 Japan .
48-99176 9/1973 Japan .
994890 6/1965 United Kingdom .
1377676 12/1974 United Kingdom .

Primary Examiner—Dolph H. Torrence
Attorney, Agent, or Firm—Cushman, Darby & Cushman

[57] ABSTRACT

A method for the preparation of a liquid diphenylmethane diisocyanate composition which comprises reacting one molar proportion of substantially pure 4,4'-diphenylmethane diisocyanate, as hereinbefore defined, with from 0.01 to 0.8 molar proportions of a monoalkoxy polyalkylene glycol of the formula:

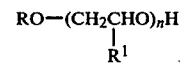

wherein R represents an alkyl group containing from 1 to 12 carbon atoms, $R^1$ represents hydrogen or an alkyl group containing from 1 to 3 carbon atoms and n is an integer of from 2 to 58, the reaction being performed at a temperature of from 100° to 250° C. and in the presence of a catalyst for the NCO/OH reaction.

The liquid diisocyanate compositions are useful in the manufacture of polyurethanes, especially elastomers and flexible foams.

4 Claims, No Drawings

LIQUID POLYISOCYANATE COMPOSITIONS

This invention relates to liquid polyisocyanate compositions and in particular to compositions containing diphenylmethane diisocyanate and to the use of such compositions in the manufacture of polyurethanes.

It is well known to manufacture polyurethanes, of a cellular or non-cellular nature, by reacting an organic polyisocyanate with an organic polyol in the presence of additives of various kinds. Many organic polyisocyanates have been proposed for use in making polyurethanes but, since many polyurethane manufacturing processes involve the rapid mixing of materials at room temperature, it is preferred to use polyisocyanates that are liquid at room temperature and that remain in the liquid state without significant deposition of solid materials even when stored at relatively low temperatures such as may be encountered in winter.

One of the polyisocyanates which has been used commercially in the manufacture of polyurethanes is diphenylmethane diisocyanate which is generally available in various forms. For the manufacture of high grade polyurethane elastomers, the preferred form is substantially pure 4,4'-diphenylmethane diisocyanate which, for present purposes means diphenylmethane diisocyanate containing at least 97% by weight of the 4,4'-isomer, any impurity being largely the 2,4'-isomer with traces of the 2,2'-isomer.

Substantially pure 4,4'-diphenylmethane diisocyanate is not a liquid at room temperature, however, having a melting point of about 40° C. For use in polyurethane manufacture, therefore, it is necessary to melt this material and maintain it in a molten condition. In order to overcome this difficulty, various proposals have been made for converting substantially pure 4,4'-diphenylmethane diisocyanate to a liquid polyisocyanate composition which remains liquid when stored at a low temperature.

The present invention provides a method for the preparation of a liquid diphenylmethane diisocyanate composition which comprises reacting one molar proportion of substantially pure 4,4'-diphenylmethane diisocyanate, as hereinbefore defined, with from 0.01 to 0.8 molar proportions of a monoalkoxy polyalkylene glycol of the formula:

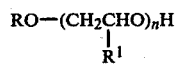

wherein R represents an alkyl group containing from 1 to 12 carbon atoms, $R^1$ represents hydrogen or an alkyl group containing from 1 to 3 carbon atoms and n is an integer of from 2 to 58, the reaction being performed at a temperature of from 100° to 250° C. and in the presence of a catalyst for the NCO/OH reaction.

In the monoalkoxy polyalkylene glycol, R is preferably an alkyl group containing from 1 to 5 carbon atoms, for example methyl or ethyl. $R^1$ is preferably hydrogen or methyl, the material then being a monoalkoxy polyethylene or polypropylene glycol. The above formula includes copolymeric monoalkoxy polyalkylene glycols, for example copolymers derived from ethylene and propylene oxides. The integer n is preferably less than 44. Mixtures of monoalkoxy polyalkylene glycols may be used.

Under the conditions specified for the performance of the method of the invention, the urethane formed by the reaction of monoalkoxy polyalkylene glycol with the diphenylmethane diisocyanate reacts with further isocyanate to form an allophanate. It will be appreciated, however, that the reaction product may contain a minor proportion of material that has not reacted beyond the urethane stage as well as higher functionality material where the reaction has gone beyond the allophanate stage.

Particularly useful products are obtained when one molar proportion of the substantially pure 4,4'-diphenylmethane diisocyanate is reacted with from 0.1 to 0.3 molar proportions of the monoalkoxy polyalkylene glycol.

The reaction between the diphenylmethane diisocyanate and the monoalkoxy polyalkylene glycol is preferably performed at a temperature in the range 100° to 200° C. and is continued until a product of the desired constitution is obtained. The reaction catalyst may be any catalyst known for the reaction between isocyanate and hydroxyl groups. Particularly suitable catalysts are tin and dialkyl tin salts of carboxylic acids, for example stannous octoate and dibutyl tin dilaurate. Other suitable catalysts are tertiary amines in which the nitrogen atom is not directly attached to an aromatic residue, for example 1,4-diazabicyclo[2.2.2]octane. The monoalkoxypolyalkylene glycol is conveniently added slowly to the polyisocyanate and catalyst at the reaction temperature, but the reactants may alternatively be brought together at ambient temperature or at an intermediate temperature and then heated to the reaction temperature. After the reaction is complete, it is preferable to deactivate the catalyst either chemically, for example by incorporating an acidic substance, or physically, for example by adsorption on to activated carbon. It is also possible in some cases to remove the catalyst by filtration or distillation.

The polyisocyanate compositions of the present invention are liquid compositions which are stable to storage, that is to say the compositions remain liquid at room temperature for long periods of time, sufficient in fact for all practical purposes, and can be transported or stored at low temperature without significant sedimentation of crystals of 4,4'-diphenylmethane diisocyanate. The compositions are suitable for use in the manufacture of polyurethanes using techniques fully described in the prior art. Being substantially difunctional, the compositions are particularly suitable for the manufacture of polyurethane elastomers and flexible foams including microcellular elastomers.

If desired, the choice of monoalkoxypolyalkylene glycol may be made with a view to tailoring the properties of the composition to suit a particular application. For example, in the formation of polyurethane foams from aqueous systems it may be desirable to increase the interaction between the aqueous phase and the isocyanate phase; this may be achieved by employing a hydrophilic monoalkoxypolyalkylene glycol such as a monoalkoxypolyethylene glycol. If less interaction between the phases is required, a more hydrophobic material such as a monoalkoxypolypropylene glycol may be more suitable.

In general we have found that the compositions of the present invention give superior polyurethane foam products, in terms of properties such as strength and ease of cure, when compared with 4,4'-diphenylmethane diisocyanate in which no reaction with a monoalkoxy polyalkylene glycol has taken place.

The invention is illustrated by the following Examples in which all parts and percentages are by weight unless otherwise stated.

EXAMPLE 1

To 250 parts of molten 4,4'-diphenylmethane diisocyanate was added 0.5 part of dibutyl tin dilaurate and the mixture was stirred under dry nitrogen. The temperature was raised with stirring to 120° C. at which point 40 parts of mono methoxy polyethylene glycol of molecular weight 246 were added slowly over 15 minutes whilst maintaining the temperature at 120° C. The reaction mixture was stirred for another 2 hours at 120° C. and then cooled to ambient temperature. The product was a light brown liquid having an isocyanate content of 23.6%. The isocyanate content of the 4,4'-diphenylmethane diisocyanate starting material is 33.6% indicating that approximately 20% of the original isocyanate groups had reacted.

Water blown flexible foam mouldings were prepared from the product and also from unmodified 4,4'-diphenylmethane diisocyanate using the conventional methods known in the art and the following formulation:

|  | Parts by weight | |
|---|---|---|
|  | Foam A | Foam B |
| Oxypropylated glycerol with 15% ethylene oxide tip 5,250 molecular weight | 100 | 100 |
| Water | 3.4 | 3.4 |
| DABCO 33LV (ex Air Products & Chem.) | 0.4 | 0.4 |
| Niax catalyst A1 (ex Union Carbide) | 0.1 | 0.1 |
| Silicone B4113 (ex Union Carbide) | 0.1 | 0.1 |
| Refrigerant 11 | 2.0 | 2.0 |
| Isocyanate product prepared as described above | — | 64.2 |
| Pure 4,4'-diisocyanato diphenylmethane (molten) | 45.1 | — |

Foam A was a crumbly, cheesy mass, Foam B was a good quality, resilient foam and had the following physical properties:

| Overall density (kg/m$^3$) | 64 |
|---|---|
| Elongation % | 115 |
| Tensile strength (kN/m$^2$) | 150 |
| Tear strength (N/m) | 605 |
| Compression 25% | 7.5 |
| Hardness 40% | 10.4 |
| (kN/m$^2$) 50% | 13.8 |
| 65% | 28.4 |

EXAMPLE 2

To 860 parts of molten 4,4'-diphenylmethane diisocyanate were added 1.7 parts of dibutyl tin laurate and the mixture was stirred under dry nitrogen. The temperature was raised with stirring to 120° C. at which point 140 parts of mono methoxypolypropylene glycol of molecular weight 406 were added slowly over 15 minutes whilst maintaining the temperature at 120° C. The reaction mixture was stirred for 1½ hours at 120° C. and then cooled to ambient temperature. The product was a light brown liquid having an isocyanate content of 23.7% indicating that approximately 20% of the original isocyanate groups had reacted.

EXAMPLE 3

To 788 parts of molten 4,4'-diphenylmethane diisocyanate were added 1.6 parts dibutyl tin laurate and the mixture stirred under dry nitrogen. The temperature was raised with stirring to 120° C. at which point 212 parts of monoethoxy polyethylene glycol of molecular weight 1100 were added slowly over 15 minutes whilst maintaining the temperature at 120° C. The reaction mixture was stirred for 1½ hours at 120° C. and then cooled to ambient temperature. The product was a light brown liquid having an isocyanate value of 21.3% indicating that approximately 20% of the original isocyanate groups had reacted.

Cup foam elastomers were prepared by mixing 42.4 parts of this product and 100 parts of the following resin blend:

85.9 parts—Polyol 1*
8.6 parts—1,4-butane diol
0.4 parts—catalyst DABCO
0.0007 parts—Tin catalyst Foamrez ULI
0.18 parts—water
5.5 parts—Arcton 11

*Polyol 1 is a mixture of 0.34 parts ethylene glycol, 29.86 parts oxyalkylated diethylene glycol of hydroxyl value 30.0 mg KOH/gm and 59.8 parts of oxyalkylated mixture of 60/40 glycerol/diethylene glycol of hydroxyl value 29 mg KOH/gm.

The elastomers obtained had high tensile and tear strengths, compared with pure 4,4'-diphenylmethane diisocyanate which gave a crumbly soft very poor elastomer.

EXAMPLE 4

To 926 parts of 4,4'-diphenylmethane diisocyanate were added 1.9 parts of dibutyl tin dilaurate. The mixture was heated with stirring under dry nitrogen to 120° C. and 74 parts of ethylene glycol monomethyl ether were added slowly. The mixture was heated at 120° C. for a further 2 hours and allowed to cool. The product was a clear brown liquid with an isocyanate content of 23.0%.

Flexible foam mouldings were prepared from the products of Examples 1 and 4 using the conventional moulding methods known in the art and the following formulations.

|  | Parts by weight | |
|---|---|---|
|  | Foam C | Foam D |
| Oxypropylated glycerol with 15% ethylene oxide tip, 5250 molecular weight | 100 | 100 |
| Water | 1.8 | 1.8 |
| Niax Catalyst A1 | 0.1 | 0.1 |
| Refrigerant 11 | 10 | 10 |
| Isocyanate from Example 1 | 47.8 | — |
| Isocyanate from Example 4 | — | 46.8 |

|  | Parts by weight | |
|---|---|---|
|  | Foam E | Foam F |
| Oxypropylated glycerol with 15% ethylene oxide tip, 5250 molecular weight | 100 | 100 |
| Water | 2.6 | 2.6 |
| Dabco 33LV | 0.4 | 0.4 |
| Niax Catalyst A1 | 0.1 | 0.1 |
| Silicone B4113 | 0.1 | 0.1 |
| Oxyethylated octyl phenol | 1.0 | 1.0 |
| Refrigerant 11 | 2.0 | 2.0 |
| Isocyanate from Example 1 | 68.3 | — |
| Isocyanate from Example 4 | — | 67.3 |

Compression sets of each of the foams C, D, E, F were measured with the following results:

|  |  | Foam C | Foam D | Foam E | Foam F |
|---|---|---|---|---|---|
| Compression Set % | 50% compression | 9 | 17 | 10 | 31 |
|  | 75% compression | 9 | 59 | 12 | 64 |
|  | 90% compression | 11 | 86 | 14 | 84 |

The lower compression set values of Foams C and E relative to Foams D and F clearly demonstrate the advantage of using 4,4'-diphenylmethane diisocyanate modified with an alkyl ether of a polyalkylene glycol instead of an alkyl ether of a simple alkylene glycol.

We claim:

1. A method for the preparation of a liquid diphenylmethane diisocyanate composition which comprises reacting one molar proportion of substantially pure 4,4'-diphenylmethane diisocyanate, containing at least 97% of the 4,4' isomer and any impurity being largely the 2,4' isomer and traces of 2,2' isomer, with from 0.01 to 0.8 molar proportions of a monoalkoxy polyalkylene glycol of the formula:

$$RO-(CH_2CHO)_nH$$
$$\phantom{RO-(CH_2CH}|$$
$$\phantom{RO-(CH_2CHO)_n}R^1$$

wherein R represents an alkyl group containing from 1 to 12 carbon atoms, $R^1$ represents hydrogen or an alkyl group containing from 1 to 3 carbon atoms and n is an integer of from 2 to 58, the reaction being performed at a temperature of from 100° to 250° C. and in the presence of a catalyst for the NCO/OH reaction whereby the urethane formed by the reaction of the monoalkoxy polyalkylene glycol with the diisocyanate reacts with further diisocyanate to form a major proportion of allophanate.

2. A method according to claim 1 wherein R is an alkyl group containing from 1 to 5 carbon atoms.

3. A method according to claim 1 or claim 2 wherein $R^1$ is hydrogen or methyl.

4. A method according to claim 1 or claim 2 wherein the diphenylmethane diisocyanate is reacted with from 0.1 to 0.3 molar proportions of the monoalkoxy polyalkylene glycol.

* * * * *